United States Patent [19]

Yokota et al.

[11] Patent Number: 5,776,948
[45] Date of Patent: Jul. 7, 1998

[54] FLUOROQUINOLINE DERIVATIVE

[75] Inventors: Takeshi Yokota, Chiba; Masayuki Haramura, Shizuoka; Akira Okamachi, Shizuoka; Toshihiko Makino, Shizuoka, all of Japan

[73] Assignee: Chugai Seiyaku Kabushiki Kaisha, Tokyo, Japan

[21] Appl. No.: 728,431

[22] Filed: Oct. 9, 1996

Related U.S. Application Data

[63] Continuation of Ser. No. 411,802, filed as PCT/JP93/01460 Oct. 12, 1993.

[30] Foreign Application Priority Data

Oct. 9, 1992 [JP] Japan .................. 4-312588

[51] Int. Cl.$^6$ .................. A61K 31/47; C07D 215/233; C07D 215/18; C07D 215/56
[52] U.S. Cl. .................. 514/312; 546/156
[58] Field of Search .................. 546/156; 514/312

[56] References Cited

U.S. PATENT DOCUMENTS

| | | | |
|---|---|---|---|
| 4,880,814 | 11/1989 | Chu | 514/300 |
| 4,929,613 | 5/1990 | Culbertson | 514/210 |
| 4,945,160 | 7/1990 | Kiely | 540/481 |
| 5,039,682 | 8/1991 | McGuirk | 514/312 |
| 5,137,892 | 8/1992 | Chu | 514/278 |
| 5,527,910 | 6/1996 | Kim | 546/156 |
| 5,545,642 | 8/1996 | Petersen | 514/312 |
| 5,597,923 | 1/1997 | Nagano | 546/156 |

FOREIGN PATENT DOCUMENTS

| | | |
|---|---|---|
| 1-93573 | 4/1989 | Japan . |
| 1-254666 | 10/1989 | Japan . |

OTHER PUBLICATIONS

Domagala, J of Medicinal Chemistry, vol. 29, No. 4, pp. 445–448, 1986.
Sanchez, J of Medicinal Chemistry, vol. 31, No. 5, pp. 983–991, 1988.

Chemical Abstracts, abstract No. 174003d, Preparation of 4-quinolinone-4-carbxylates as Medical Bacterides, vol. 111 No. 19, pp. 714–715, Nov. 6, 1989.

Chemical Abstracts, abstract No. 185293m, Antibacterial Quinoline Derivatives and Their Salts, vol. 114, No. 19, May 13, 1991.

Primary Examiner—C. Warren Ivy
Assistant Examiner—D. Margaret M. Mach
Attorney, Agent, or Firm—Browdy and Neimark

[57] ABSTRACT

Antibacterial fluoroquinoline derivatives and salts thereof of the following formula are stable and have low toxicity and high photostability and low cytotoxicity under light irradiation:

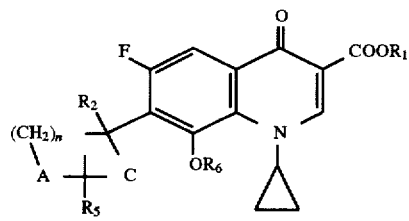

wherein $R_1$ is hydrogen or lower alkyl;

$R_2$ is hydrogen, optionally protected amino, optionally protected aminocarbonyl or optionally protected carboxyl;

$R_5$ is halogen, lower alkyl or optionally protected hydroxyl or is the same as $R_2$;

$R_6$ is lower alkyl;

A is $CH_2$, optionally protected nitrogen or oxygen;

and n and m are each an integer of from 0 to 4, provided that n+m is an integer of from 1 to 4.

8 Claims, No Drawings

FLUOROQUINOLINE DERIVATIVE

This application is a continuation of application Ser. No. 08/411,802, filed Apr. 10, 1995, which is a 371 of PCT/JP93/01460, filed Oct. 12, 1993.

This invention relates to a novel fluoroquinoline derivative represented by the general formula (1):

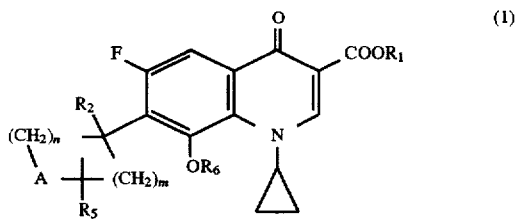

wherein $R_1$ represents a hydrogen or a lower alkyl;

$R_2$ represents hydrogen, optionally protected amino, optionally protected aminocarbonyl or optionally protected carboxyl;

$R_5$ represents halogen, lower alkyl or optionally protected hydroxyl or has the same meaning as that of $R_2$, each capable of substituting arbitrary carbon;

$R_6$ represents lower alkyl;

A represents $CH_2$, optionally protected nitrogen or oxygen; and n and m are each an integer of from 0 to 4, provided that n+m is an integer of from 1 to 4; and its salt.

The compound represented by the general formula (1) shows a well-balanced antibacterial activity on both gram-positive and gram-negative bacteria. When orally or parenterally administered, it achieves a high concentration in the blood. Also, it is a stable chemical having a low toxicity and a high photostability and exhibiting a low cytotoxicity under light irradiation. Accordingly, this compound is highly useful as a drug such as an antibacterial agent.

BACKGROUND ART

There have been widely employed quinoline antimicrobial agents such as norfloxacin, enoxacin, ofloxacin, etc. in clinical medicine. Each of these compounds is a drug suitable for oral administration but unsuitable for parenteral administration because of its poor solubility under physiological conditions.

In addition to the above-described ones, there have been known a number of quinolone antibacterial agents [see, for example, Japanese Patent Application Laid-Open (Kokai) Nos. Sho-59-67269, ibid. Sho-59-212474, ibid. Sho-60-214773, ibid. Sho-62-252772 and ibid. Sho-63-198664). However, these compounds are also unsuitable for parenteral administration and there have been known few drugs which are satisfactory in both of antibacterial activity and safety. Thus there has been a requirement to develop a novel synthetic antibacterial agent.

On the other hand, effects of quinolone antibacterial agents on the skin have attracted public attention. In particular, a photolytic product of such a compound has a toxicity about 10 times or more as high as that of the original compound and, further, an enhanced cytotoxicity [see Antimicrobial Agents and Chemotherapy, 36 (8), 1715 –1719 (1992)]. In the development of a novel drug, therefore, it is also necessary to be careful about the systemic toxicity of its photolytic product.

DISCLOSURE OF THE INVENTION

Under these circumstances, the present inventors have conducted extensive studies in order to develop an excellent antibacterial agent. As a result, they have successfully found out that the above object can be achieved by using a compound represented by the general formula and its salt and thus completed the present invention.

The protecting groups of the optionally protected amino or optionally protected aminocarbonyl in the definition of $R_2$ or $R_5$ in the general formula (1) are exemplified by those commonly employed in the art. Examples thereof include acyl groups which are liable to leave such as trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, acetyl, (mono-, di-, tri-)chloroacetyl, trifluoroacetyl, formyl, t-amyloxycarbonyl, t-butoxycarbonyl, p-methoxybenzyloxy-carbonyl, 3,4-dimethoxybenzyloxycarbonyl, 4-(phenyl-azo) benzyloxycarbonyl, 4-(4-methoxyphenylazo)benzyloxycarbonyl, pyridin-1-oxide-2-yl-methoxycarbonyl, 2-furyloxycarbonyl, diphenylmethoxycarbonyl, 1,1-dimethylpropoxy-carbonyl, isopropoxycarbonyl, 1-cyclopropylethoxycarbonyl, phthaloyl, succinyl, 1-adamantyloxycarbonyl and 8-quinolyl-oxycarbonyl groups, those which are liable to leave such as triethyl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxy-phenyl)carbamoyl]-2-propylidene, 1-[N-(4-methoxy-phenyl)carbamoyl]-2-propylidene, 2-ethoxycarbonylcyclo-hexylidene, 2-ethoxycarbonylcyclopentylidene, 2-acetyl-cyclohexylidene and 3,3-dimethyl-5-oxocyclohexylidene groups, (di-, tri- )alkylsilyl groups and lower alkyl groups such as methyl and ethyl groups.

The optionally protected carboxyl is exemplified by those commonly employed as a protected carboxyl group. Examples thereof include those protected by methyl, ethyl, n-propyl, i-propyl, n-butyl, t-butyl, s-butyl, benzyl, diphenylmethyl, trityl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthal-imidomethyl, trichloroethyl, 1,1-dimethyl-2-propenyl, 1,1-dimethylpropyl, acetoxymethyl, propionyloxymethyl, pivaloyl-oxymethyl, 3-methyl-3-butynyl, succinimidomethyl, 1-cyclopropylethyl, methylsulfenylmethyl, phenylthiomethyl, dimethylaminomethyl, quinoline-1-oxide-2-methyl, pyridin-1-oxide-2-yl-methyl and bis(p-methoxyphenyl) methyl, and those protected with a nonmetal compound such as titanium tetrachloride.

The salt of the compound represented by the general formula (1) is exemplified by those with commonly known basic groups such as amino groups or acidic groups such as carboxyl groups. Examples of salts with basic groups such as amino groups include salts with mineral acids such as hydrochloric acid and sulfuric acid, those with organic carboxylic acids such as oxalic acid, formic acid, trichloroacetic acid and trifluoroacetic acid and those with sulfonic acids such as methanesulfonic acid, p-toluenesulfonic acid and naphthalenesulfonic acid. Examples of the salts with acidic groups such as carboxyl group include salts with alkali metals such as sodium and potassium, salts with alkaline earth metals such as calcium and magnesium, ammonium salts, those with nitrogen-containing organic bases such as dibenzylamine, N-benzyl-p-phenethylamine, 1-ephen-amine and N,N-dibenzylethylenediamine, and triethylamine, trimethylamine, tributylamine, pyridine, dimethylaniline, N-methylpiperidine, N-methylmorpholine, diethylamine and dicyclohexylamine salts.

In the present invention, the term "lower alkyl" means an alkyl group having 1 to 6 carbon atoms and preferably exemplified by methyl, ethyl, n-propyl, i-propyl, n-butyl, i-butyl, s-butyl and t-butyl groups.

When the compound represented by the general formula (1) and its salt occur in the form of isomers, all of these isomers are involved in the scope of the present invention.

Best Mode for Carrying Out the Invention

The compound represented by the general formula (1) and its salt, which are novel compounds and have never been described in any literature, can be produced by, for example, the following method.

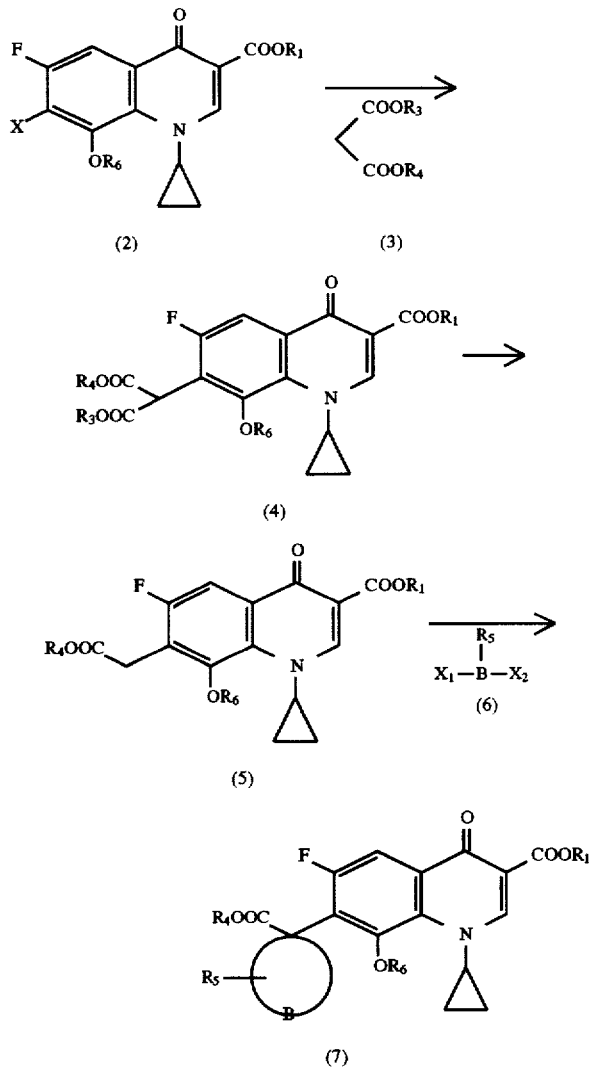

wherein $R_1$, $R_2$, $R_5$ and $R_6$ are each as defined above;

$R_3$ and $R_4$ may be either the same or different and each represents a carboxy-protecting group;

X represents halogen;

$X_1$ and $X_2$ may be either the same or different and each represents a leaving group; and B represents $-(CH_2)_p-$, $-(CH_2)_m-O-(CH_2)_n-$ or

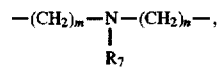

wherein $R_7$ represents hydrogen or an amino-protecting group; and n and m are each an integer of from 0 to 4, provided that n+m is an integer of from 1 to 4.

In the above synthesis method, the step for obtaining the compound of the general formula (5) from the compound of the general formula (2) can be effected in accordance with the method described in U.S. Pat. No. 3,590,036. Namely, the compound of the general formula (2) is reacted with the compound of the general formula (3) or its salt to thereby give the compound of the general formula (4) or its salt. After deblocking and decarboxylating the obtained compound in a conventional manner, a carboxy-protecting group is introduced thereinto.

Examples of the active methylene of the compound of the general formula (3) and the active methylene salt of the compound of the general formula (4) include salts of alkali metals such as sodium and potassium.

The step for obtaining the compound of the general formula (7) from the compound of the general formula (5) can be effected by reacting the compound of the general formula (5) or its salt with the compound of the general formula (6) or its salt in an appropriate solvent optionally in the presence of a base.

Examples of the leaving groups $X_1$ and $X_2$ in the general formula (6) include halogen atoms such as chlorine, bromine and iodine atoms, alkanesulfonyloxy groups such as methanesulfonyloxy group, and arenesulfonyloxy groups such as toluenesulfonyloxy group.

Any solvent may be used herein without restriction, so long as it remains inert during the reaction. Preferable examples thereof include alcohols such as methanol, ethanol and 2-propanol, ethers such as diethyl ether, tetrahydrofuran and dioxane, aromatic hydrocarbons such as benzene, toluene and xylene, amides such as N,N-dimethylformamide and N,N-dimethylacetamide, sulfoxides such as dimethylsulfoxide and water. Also, a mixture of two or more of these solvents may be used therefor.

Examples of the base include inorganic bases such as alkali hydroxides, alkali hydrogencarbonates and alkali carbonates, metal hydrides such as sodium hydride and potassium hydride, metal alkoxides such as sodium ethoxide and sodium methoxide, and organic bases such as 1,8-diazabicyclo-[5,4,0]undec-7-ene (DBU). In general, such a base is used at least in an equimolar amount, preferably 1 to 5 times by mol as much, with the compound of the general formula (5).

The compound of the general formula (6) or its salt is used at least in an equimolar amount, preferably 1 to 5 times by mol as much, with the compound of the general formula (5) or its salt.

The reaction temperature ranges from 0° C. to the boiling point of the solvent employed, preferably from 20 to 100° C. The reaction is carried out usually for 30 minutes to 50 hours, preferably for 3 to 20 hours.

After deblocking the compound of the general formula (7) or its salt, the deblocked compound may be further subjected to a reaction publicly known per se, for example, decarboxylation, reduction or transfer reaction to thereby give the compound of the general formula (1) or its salt.

The compounds represented by the general formulae (4), (5) and (7) or salts thereof are novel compounds per se and constitute a part of the present invention.

Alternatively, the compound represented by the general formula (1) or its salt can be obtained by the following method.

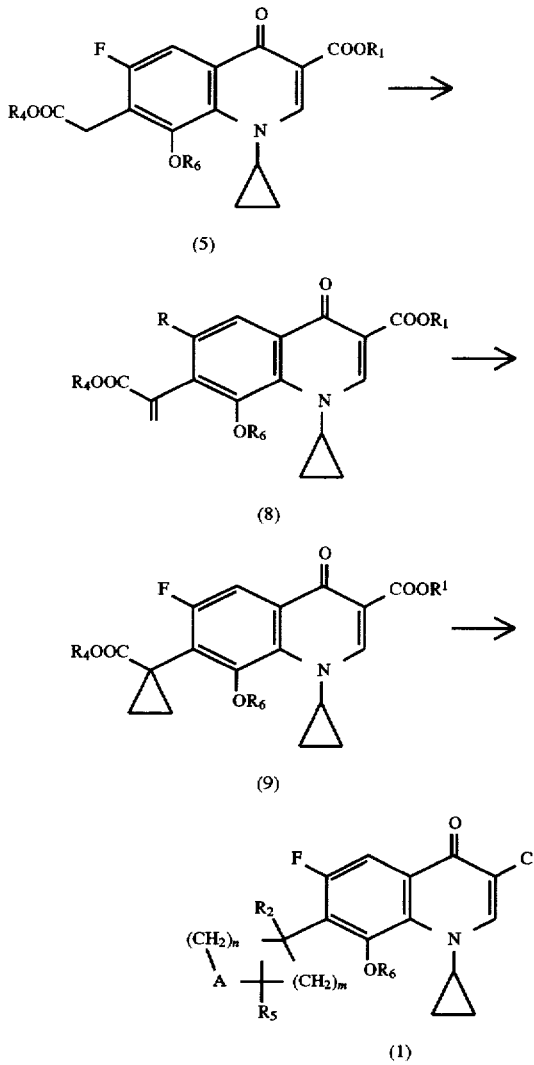

wherein $R_1$, $R_2$, $R_4$, $R_5$, $R_6$, A, m and n are each as defined above.

The step for obtaining the compound of the general formula (8) form the compound of the general formula (5) may be carried out by treating the compound of the general formula (5) by the method described in Chem. Ber., 99, 2408 (1966).

The compound of the general formula (8) or its salt is reacted with, for example, trimethylsulfoxonium iodide in the presence of a base. Thus the compound of the general formula (9) or its salt can be obtained.

Examples of the base to be used herein include metal hydrides such as sodium hydride and potassium hydride.

The compound of the general formula (9) or its salt can be derived into the compound of the general formula (1) or its salt via, for example, deblocking and decarboxylation, reduction or transfer reaction.

Alternatively, the compound of the general formula (9) can be obtained from the compound of the general formula (8) by the Simmons-Smith reaction or the 1,3-dipole addition reaction.

Examples of the solvent to be used herein include ethers such as diethyl ether, tetrahydrofuran and dioxane, and aromatic hydrocarbons such as benzene, toluene and xylene.

The compounds represented by the general formulae (8) and (9) or salts thereof are novel compounds per se and constitute a part of the present invention.

Alternatively, the compound represented by the general formula (1) or its salt can be obtained by the following method.

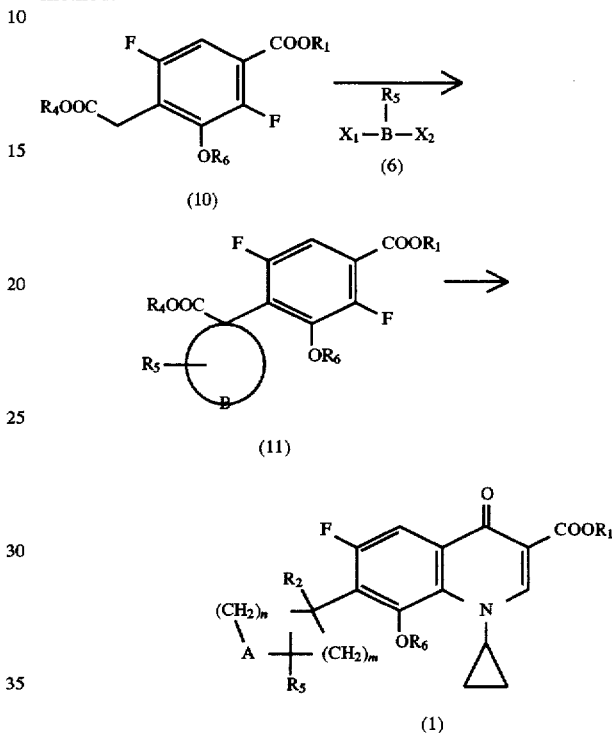

wherein $R_1$, $R_2$, $R_4$, $R_5$, $R_6$, A, B, $X_1$, $X_2$, m and n are each as defined above.

The compound of the general formula (11) or its salt can be derived from the compound of the general formula (10) by a method similar to the one for obtaining the compound (7) from the compound (5).

The compound of the general formula (11) or its salt can be derived into the compound of the general formula (1) or its salt by, for example, the method in accordance with Angew. Chem. Int. Ed. Engl., 18, 72 (1979).

The compound represented by the general formula (1) or its salt thus obtained can be isolated and purified in a conventional manner.

To use the compound according to the present invention as a medicine, it may be processed into tablets, capsules, dusts, syrups, granules, suppositories, ointments, injections, etc. by a conventional method with the use of carriers commonly employed in the art. The dose, route and frequency of the administration may be appropriately selected depending on the conditions of a patient. Usually, it may be orally or parenterally (for example, injections, eye drops, rectal preparations) administered to an adult in a dose of from 0.1 to 100 mg/kg/day once to several times.

EXAMPLES

To further illustrate the present invention in greater detail, and not by way of limitation, the following Examples will be given.

Example 1

Synthesis of ethyl 1-cyclopropyl-7-diphenylmethoxycarbonyl-methyl-6-fluoro-8-methoxy-1,4-dihydro-4-oxo-3-guinoline-carboxylate 30.7 g of sodium hydride was suspended in 1.8 l of N,N-dimethylformamide and 261 g of di-t-butyl malonate was dropped thereinto over 2 hours under ice-cooling. After the completion of the addition, 100 g of ethyl 1-cyclopropyl-6,7-difluoro-8-methoxy-1,4-dihydro-4-oxo-3-quinolone-carboxylate was added thereto. Then the mixture was stirred successively at 50° to 60° C. for 3 hours, at room temperature for 12.5 hours, at 50° to 60° C. for 11 hours and at room temperature for 14 hours. Next, conc. hydrochloric acid was added thereto under ice-cooling to thereby regulate the pH value of the mixture to 1. After adding ethyl acetate and water, the organic layer was collected, successively washed with water and a saturated aqueous solution of sodium hydro-gencarbonate and dried over anhydrous sodium sulfate. After removing the solvent under reduced pressure, diisopropyl ether was added to the obtained residue and the solid thus precipitated was collected by filtration. To the solid thus obtained, 500 ml of methylene chloride and 500 ml of tri-fluoroacetic acid were added. Then the mixture was stirred at room temperature for 66 hours. After removing the solvent under reduced pressure, diethyl ether was added to the obtained residue and the solid thus precipitated was collected by filtration. The solid thus obtained was suspended in 700 ml of methylene chloride and 300 ml of methanol. Then a diphenyldiazomethane-dichloromethane solution was dropped thereinto until the color of the mixture did not fade any more. Then the excessive diphenyldiazomethane was decomposed with acetic acid and the solvent was removed under reduced pressure. To the obtained residue, diethyl ether was added. The solid thus precipitated was collected by filtration. Thus 96.7 g of ethyl 1-cyclopropyl-7-diphenylmethoxycarbonylmethyl-6-fluoro-8-methoxy-1,4-dihydro-4-oxo-3-quinolinecarboxylate was obtained (yield: 59.0%).

NMR (CDCl$_3$) δ: 0.77–1.20 (4H,m), 1.35 (3H,t,J=7 Hz), 3.54 (3H,s), 3.62–4.06 (3H,m), 4.30 (1H,q,J=7 Hz), 6.77 (1H,s), 7.05 (1OH,s), 7.80 (1H,d,J=9 Hz), 8.55 (1H,s).

Ms m/e 529 (M$^+$).

Example 2

Synthesis of ethyl 1-cyclopropyl-7-(1-diphenylmethoxycarbonylvinyl)-6-fluoro-8-methoxy-1,4-dihydro-4-oxo-3-quinoline-carboxylate 2.64 g of ethyl 1-cyclopropyl-7-diphenylmethoxycarbonylmethyl-6-fluoro-8-methoxy-1,4-dihydro-4-oxo-3-quino-linecarboxylate was suspended in 20 ml of dimethylsulfoxide. Then 0.85 g of a 35% aqueous solution of formaldehyde and 21 mg of sodium hydrogencarbonate were added thereto and the mixture was stirred at 50° C. for 1.5 hours. To the reaction mixture, 100 ml of ethyl acetate and 50 ml of water were added and then the organic layer was collected. The organic layer thus collected was successively washed with water and a saturated aqueous solution of sodium chloride and dried over anhydrous sodium sulfate. After removing the solvent under reduced pressure, the obtained residue was dissolved in 25 ml of methylene chloride. Under ice-cooling, 0.57 g of methanesulfonyl chloride and 1.0 mg of triethylamine were successively dropped thereinto slowly and the resulting mixture was stirred at room temperature for 3 hours. 20 ml of water was added to the reaction mixture and the pH value of the mixture was regulated to 1 with 2N hydrochloric acid. Then the organic layer was collected, successively washed with water and a saturated aqueous solution of sodium chloride and dried over anhydrous sodium sulfate. After removing the solvent under reduced pressure, the oily product thus obtained was crystallized by adding ethanol and the crystals were collected by filtration. Thus 1.98 g of ethyl 1-cyclopropyl-7-(1-diphenylmethoxycarbonylvinyl)-6-fluoro-8-methoxy-1,4-dihydro-4-oxo-3-quinolinecarboxylate was obtained (yield: 73.1%).

NMR (CDCl$_3$) δ: 0.78–1.20 (4H,m), 1.37 (3H,t,J=7 Hz), 3.55 (3H,s), 3.60–4.00 (1H,m), 4.33 (2H,q,J=7 Hz), 6.02 (1H,s), 6.77 (1H,s), 6.92 (1H,s), 7.20 (1OH,s), 7.89 (1H,d,J=9 Hz), 8.52 (1H,s).

Ms m/e 541 (M$^+$).

Example 3

Synthesis of ethyl 1-cyclopropyl-7-(1-diphenylmethoxycar- bonylcyclopropyl)-6-fluoro-8-methoxy-1,4-dihydro-4-oxo-3- guinolinecarboxylate 160 mg of 60% sodium hydride was suspended in 18 ml of N,N-dimethylformamide and 877 mg of trimethylsulfoxonium iodide was added thereto under ice-cooling. After stirring at room temperature for 40 minutes, 1.80 g of ethyl 1-cyclopropyl-7-(1-diphenylmethoxycarbonylvinyl)-6-fluoro-8-methoxy-1,4-dihydro-4-oxo-3-quinolinecarboxylate was added thereto and the resulting mixture was stirred at 50° C. for 3 hours. To the reaction mixture, 30 ml of ethyl acetate and 15 ml of water were added and the pH value of the mixture was regulated to 1 with 2N hydrochloric acid. Then the organic layer was collected, successively washed with water and a saturated aqueous solution of sodium chloride and dried over anhydrous sodium sulfate. After removing the solvent under reduced pressure, the residue thus obtained was crystallized by adding ethyl acetate/n-hexane and the crystals were collected by filtration. Thus 497 mg of ethyl 1-cyclopropyl-7-(1-diphenylmethoxycarbonylcyclopropyl)-6- fluoro-8-methoxy-1,4-dihydro-4-oxo-3-quinolinecarboxylate was obtained (yield: 26.9%).

NMR (CDCl$_3$) δ: 0.80–2.00 (8H,m), 1.35 (3H,t,J=7 Hz), 3.52 (3H,s), 3.60–4.05 (1H,m), 4.30 (2H,1,J=7 Hz), 6.82 (1H,s), 7.10 (1OH,s), 7.82 (1H,d,J=10 Hz), 8.50 (1H,s).

Ms m/e 555 (M$^+$).

Example 4

Synthesis of ethyl 1-cyclopropyl-7-(1-diphenylmethoxycarbonylcyclopentyl)-6-fluoro-8-methoxy-1,4-dihydro-4-oxo-3-quinolinecarboxylate 10 g of ethyl 1-cyclopropyl-7-diphenylmethoxycarbonylmethyl-6-fluoro-8-methoxy-1,4-dihydro-4-oxo-3-quinolinecarboxylate was dissolved in 300 ml of N,N-dimethylform-amide and 1.89 g of 60% sodium hydride was added thereto under ice-cooling. After stirring for 45 minutes, 5.43 g of 1,4-dibromobutane was added thereto and the resulting mixture was stirred at room temperature for 20 hours. After regulating the pH value of the mixture to 5 with 2N hydro-chloric acid, 100 ml of ethyl acetate, 100 ml of diethyl ether and 100 ml of water were added thereto. Then the organic layer was collected, successively washed with water and a saturated aqueous solution of sodium hydrogencarbonate and dried over anhydrous sodium sulfate. After removing the solvent under reduced pressure, diisopropyl ether was added to the crystalline product thus obtained followed by the collection of the product by filtration. Thus 8.72 g of ethyl 1-cyclopropyl-7-(1-diphenylmethoxycarbonylcyclo-pentyl)-6-fluoro-8-methoxy-1,4-dihydro-4-oxo-3-quino-linecarboxylate was obtained (yield: 79.1%).

NMR (CDCl$_3$)δ: 0.35–1.30 (4H,m), 1.35 (3H,t,J=7 Hz), 1.55–3.10 (8H,m), 3.32 (3H,s), 3.48–3.82 (1H,m), 4.31 (2H,q,J=7 Hz), 6.74 (1H,s), 7.15 (10H,s), 7.78 (1H,d,J=12 Hz), 8.45 (1H,s).

Ms m/e 583 (M$^+$).

Example 5

Synthesis of ethyl 1-cyclopropyl-7-(1-diphenylmethoxycar-bonylcyclohexyl)-6-fluoro-8-methoxy-1,4-dihydro-4-oxo-3-quinolinecarboxylate The procedure of Example 4 was repeated to thereby give ethyl 1-cyclopropyl-7-(1-diphenylmethoxycarbonylcyclohexyl)-6-fluoro-8-methoxy-1,4-dihydro-4-oxo-3-quinolinecar-boxylate.

NMR (CDCl$_3$) δ: 0.40–1.00 (4H,m), 1.37 (3H,t,J=7 Hz), 1.33–1.73 (6H,m), 2.08–2.53 (4H,m), 3.36 (3H,s), 3.25–3.79 (1H,m), 4.25 (2H,q,J=7 Hz), 6.78 (1H,s), 7.21 (10H,s), 7.75 (1H,d,J=14 Hz), 8.47 (1H,s).

Fab-Ms m/e 598 (M+H)$^+$.

Example 6

Synthesis of ethyl 1-cyclopropyl-7-(4-(diphenylmethoxycarbonyl)-2,3,5,6-tetrahydropyran-4-yl)-6-fluoro-8-methoxy-l14-dihydro-4-oxo-3-guinolinecarboxylate The procedure of Example 4 was repeated to thereby give ethyl 1-cyclopropyl-7-{4-(diphenylmethoxycarbonyl)-2,3,5,6-tetrahydropyran-4-yl}-6-fluoro-8-methoxy-1,4-dihydro-4-oxo-3-quinolinecarboxylate.

NMR (CDCl$_3$) δ: 0.57–1.20 (4H,m), 1.38 (3H,t,J=7 Hz), 2.25–2.70 (4H,m), 3.47 (3H,s), 3.42–3.89 (2H,m),4.35 (2H,q,J=7 Hz), 6.91 (1H,s), 7.27 (10H,s), 7.78 (1H,d,J=13 Hz), 8.58 (1H,s).

Fab-Ms m/e 600 (M+H)$^+$

Example 7

Synthesis of ethyl 7-(1-carboxycyclopentyl)-1-cyclopropyl-6-fluoro-8-methoxy-1,4-dihydro-4-oxo-3-quinolinecarboxylate To 8.72 g of ethyl 1-cyclopropyl-7-(1-diphenylmethoxycarbonylcyclopentyl)-6-fluoro-8-methoxy-1,4-dihydro-4-oxo-3-quinolinecarboxylate, 50 ml of anisole and 50 ml of trifluoroacetic acid were added and the resulting mixture was stirred at room temperature for 63 hours. Then the reaction mixture was concentrated under reduced pressure and the obtained residue was crystallized by adding diethyl ether. Next, the crystals were collected by filtration. Thus 5.2 g of ethyl 7-(1-carboxycyclopentyl)-1-cyclopropyl-6-fluoro-8-methoxy-1,4-dihydro-4-oxo-3-quinolinecarboxylate was obtained (yield: 66.1%).

NMR (CDCl$_3$) δ: 0.55–1.60 (4H,m), 1.34 (3H,t,J=7 Hz), 1.63–2.33 (4H,m), 2.35–3.06 (4H,m), 3.60 (3H,s), 3.40–4.03 (1H,m), 4.33 (2H,q,J=7 Hz), 7.75 (1H,d,J=12 Hz), 8.00–8.86 (1H,m), 8.53 (1H,s).

Fab-Ms m/e 418 (M+H)$^+$.

Example 8

Synthesis of ethyl 7-(1-carboxycvclohexyl)-1-cyclopropyl-6-fluoro-8-methoxy-1,4-dihydro-4-oxo-3-quinolinecarboxylate The procedure of Example 7 was repeated to thereby give ethyl 7-(1-carboxycyclohexyl)-1-cyclopropyl-6-fluoro-8-methoxy-1,4-dihydro-4-oxo-3-quinolinecarboxylate.

NMR (DMSO-d$_6$) δ: 0.48–1.06 (4H,m), 1.30 (3H,t,J=6.82 Hz), 1.42–1.64 (6H,m), 2.04–2.20 (4H,m), 3.62 (3H,s), 3.92–4.02 (1H,m), 4.23 (2H,q,J=7.3 Hz), 7.21 (10H,s), 7.57 (1H,d,J=13.16 Hz), 8.56 (1H,s).

Ms m/e 431 (M$^+$).

Example 9

Synthesis of ethyl 7-(4-carboxy-2 3,5 6-tetrahydropyran-4-yl)-1-cyclopropyl-6-fluoro-8-methoxy-1,4-dihydro-4-oxo-3-quinolinecarboxylate The procedure of Example 7 was repeated to thereby give ethyl 7-(4-carboxy-2,3,5,6-tetrahydropyran-4-yl)-1-cyclopropyl-6-fluoro-8-methoxy-1,4-dihydro-4-oxo-3-quino-linecarboxylate.

NMR (DMSO-d$_6$) δ: 0.62–1.23 (4H,m), 1.31 (3H,t,J=6.82 Hz), 2.15–2.32 (4H,m), 3.65 (3H,s), 3.58–3.90 (4H,m), 3.90–4.13 (1H,m), 4.24 (2H,q,J=6.82 Hz), 7.59 (1H,d,J=13.16 Hz), 8.58 (1H,s).

Fab-Ms m/e 434 (M+H)$^+$.

Example 10

Synthesis of ethyl 7-(1-t-butoxycarbonylaminocyclopentyl)-1-cyclopropyl-6-fluoro-8-methoxy-1,4-dihydro-4-oxo-3-guinolinecarboxylate 4.0 g of ethyl 7-(1-carboxycyclopentyl)-1-cyclo-propyl-6-fluoro-8-methoxy-1,4-dihydro-4-oxo-3-quinolinecarboxylate was dissolved in 40 ml of methylene chloride. Under ice-cooling, 5.28 g of diphenylphosphoryl azide and 1.94 g of triethylamine were added thereto and the resulting mixture was stirred at room temperature for 14 hours. After regulating the pH value of the mixture to 7 with 2N hydro-chloric acid, the organic layer was collected, washed with water and dried over anhydrous sodium sulfate. After removing the solvent under reduced pressure, 50 ml of t-butanol was added to the obtained residue. Then the mixture was refluxed for 3.5 hours and the solvent was removed under reduced pressure. The obtained residue was purified by silica gel column chromatography (eluent: ethyl acetate:n-hexane=1:1). Thus 2.3 g of ethyl 7-(1-t-butoxycarbonylaminocyclopentyl)-1-cyclopropyl-6-fluoro-8-methoxy-1,4-dihydro-4-oxo-3-quinolinecarboxylate was obtained (yield: 49.0%).

NMR (CDCl$_3$+DMSO-d$_6$) δ: 0.55–1.40 (4H,m), 1.34 (9H,s), 1.42 (3H,t,J=7 Hz), 1.62–2.45 (8H,m), 3.73–4.12 (1H,m), 3.82 (3H,s), 4.25 (2H,q,J=7 Hz), 6.60 (1H,s), 7.67 (1H, d,J=12 Hz), 8.60 (1H,s).

Fab-Ms m/e 489 (M+H)$^+$.

Example 11

Synthesis of ethyl 7-(1-t-butoxycarbonylaminocyclohexyl)-1- cyclopropyl-6-fluoro-8-methoxy-1,4-dihydro-4-oxo-3-Quinolinecarboxylate The procedure of Example 10 was repeated to thereby give ethyl 7-(1-t-butoxycarbonylaminocyclohexyl)-1-cyclopropyl-6-fluoro-8-methoxy-1,4-dihydro-4-oxo-3-quinolinecarboxylate.

NMR (CDCl$_3$) δ: 0.62–1.87 (10H,m), 1.30 (9H,s), 2.03–2.85 (4H,m), 3.67 (3H,s), 3.80–3.982 (1H,m), 4.32 (2H,q,J=7 Hz), 5.25–5.95 (1H,brs), 7.68 (1H,d,J=13 Hz), 8.67 (1H,s).

MS m/e 502 (M$^+$).

Example 12

Synthesis of ethyl 7-(4-t-butoxycarbonylamino-2,3,5,6-tetrahydropyran-4-yl)-1-cyclopropyl-6-fluoro-8-methoxy-1,4-dihydro-4-oxo-3-guinolinecarboxylate The procedure of Example 10 was repeated to thereby give ethyl 7-(4-t-butoxycarbonylamino-2,3,5,6-tetrahydropyran-4-yl)-1-cyclopropyl-6-fluoro-8-methoxy-1,4-dihydro-4-oxo-3-quinolinecarboxylate.

NMR (DMSO-$d_6$) δ: 0.65–1.67 (8H,m), 1.32 (9H,s), 2.35–2.87 (4H,m), 3.60–4.13 (1H,m), 3.78 (3H,s), 4.34 (2H,q,J=7 Hz), 5.67(1H,brs), 7.77 (1H,d,J=14 Hz), 8.65 (1H,s).
MS m/e 504 ($M^+$).

Example 13

Synthesis of 7-(1-t-butoxycarbonylaminocyclopentyl)-1-cyclo-propyl-6-fluoro-8-methoxy-1,4-dihydro-4-oxo-3-guinolinecarboxylic acid 2.3 g of ethyl 7-(1-t-butoxycarbonylaminocyclo-pentyl)-1-cyclopropyl-6-fluoro-8-methoxy-1,4-dihydro-4-oxo-3-quinolinecarboxylate was suspended 40 ml of ethanol. Then 40 ml of a 1N aqueous solution of sodium hydroxide was added thereto and the resulting mixture was stirred at room temperature for 15 hours. After removing the solvent under reduced pressure, the mixture was acidified by adding methylene chloride and 2N HCl. The organic layer was collected, washed with water and dried over anhydrous sodium sulfate. After removing the solvent under reduced pressure, 2.2 g of 7-(1-t-butoxycarbonylaminocyclopentyl)-1-cyclo-propyl-6-fluoro-8-methoxy-1,4-dihydro-4-oxo-3-quinolinecarboxylic acid was obtained (yield: 100%).

NMR (CDCl$_3$) δ: 0.65–1.45 (4H,m), 1.31 (9H,s), 1.50–2.95 (8H,m), 3.70–4.35 (1H,m), 3.82 (3H,s), 5.70 (1H,s), 7.28 (1H,s), 7.85 (1H,d,J=12 Hz), 8.90 (1H,s).

Example 14

Synthesis of 7-(1-t-butoxycarbonylaminocyclohexyl)-1-cyclo-propyl-6-fluoro-8-methoxy-1,4-dihydro-4-oxo-3-guinolinecarboxylic acid The procedure of Example 13 was repeated to thereby give 7-(1-t-butoxycarbonylaminocyclohexyl)-1-cyclopropyl-6-fluoro-8-methoxy-1,4-dihydro-4-oxo-3-quinolinecarboxylic acid.

NMR (CDCl$_3$) δ: 0.62–1.50 (4H,m), 1.35 (9H,s), 1.47–1.92 (6H,m), 2.29–2.86 (4H,m), 3.72 (3H,s), 3.87–4.25 (1H,m), 5.22–5.52 (1H,brs), 7.75 (1H,d,J=13 Hz), 8.85 (1H,s), 10.62–11.77 (1H,brs).
MS m/e 474 ($M^+$).

Example 15

Synthesis of 7-(4-t-butoxycarbonylamino-2,3,5 6-tetrahydro-pyran-4-yll)-1-cyclopropyl-6-fluoro-8-methoxy-1,4-dihydro-4-oxo-3-guinolinecarboxylic acid The procedure of Example 13 was repeated to thereby give 7-(4-t-butoxycarbonylamino-2,3,5,6-tetrahydropyran-4-yl)-1-cyclopropyl-6-fluoro-8-methoxy-1,4-dihydro-4-oxo-3-quinolinecarboxylic acid.

NMR (CDCl$_3$) δ: 0.65–1.52 (4H,m), 1.37 (9H,s), 2.30–2.87 (4H,m), 3.67–4.27 (1H,m), 3.81 (3H,s), 7.87 (1H,d,J=13 Hz), 8.89 (1H,s), 14.20–14.67 (1H,brs).
MS m/e 476 ($M^+$).

Example 16

Synthesis of 7-(1-aminocyclopentyl)-1-cyclopropyl-6-fluoro-8-methoxy-1,4-dihydro-4-oxo-3-guinolinecarboxylic acid hydrochloride 50 ml of trifluoroacetic acid was added to 2.2 g of 7-(1-t-butoxycarbonylaminocyclopentyl)-1-cyclopropyl-6-fluoro-8-methoxy-1,4-dihydro-4-oxo-3-quinolinecarboxylic acid and the resulting mixture was stirred at room temperature for 4 hours. Then the reaction mixture was concentrated under reduced pressure and 20 ml of methanol was added thereto. After adding 10 ml of a 4N hydrochloric acid/ dioxane solution, the solvent was removed under reduced pressure. The obtained residue was crystallized by adding diethyl ether and the crystals were collected by filtration. Thus 1.7 g of 7-(1-aminocyclopentyl)-1-cyclopropyl-6-fluoro-8-methoxy-1,4-dihydro-4-oxo-3-quinolinecarboxylic acid hydrochloride was obtained (yield: 100%).

NMR (CDCl$_3$) δ: 0.67–1.50 (4H,m), 1.90–2.12 (4H,m), 2.20–2.90 (4H,m), 3.89 (3H,s), 4.12–4.27 (1H,m), 7.95 (1H,d,J=12.7 Hz), 8.98 (1H,s).
Fab-Ms m/e 361 (M+H)$^+$.

Example 17

Synthesis of 7-(1-aminocyclohexyl)-1-cyclopropyl-6-fluoro-8-methoxy-1,4-dihydro-4-oxo-3-guinolinecarboxylic acid hydrochloride The procedure of Example 16 was repeated to thereby give 7-(1-aminocyclohexyl)-1-cyclopropyl-6-fluoro-8-methoxy-1,4-dihydro-4-oxo-3-quinolinecarboxylic acid hydrochloride.

NMR (DMSO-$d_6$) δ: 0.64–2.12 (10H,m), 2.45–2.84 (4H,m), 3.84 (3H,s), 4.12–4.28 (1H,m), 7.82 (1H,d,J=13.16 Hz), 8.84 (1H,s), 8.50–8.92 (3H,brs).
MS m/e 374 ($M^+$).

Example 18

Synthesis of 7-(4-amino-2,3,5,6-tetrahydropyran-4-yl)-1-cyclopropyl-6-fluoro-8-methoxy-1,4-dihydro-4-oxo-3-guino-linecarboxylic acid hydrochloride The procedure of Example 16 was repeated to thereby give 7-(4-amino-2,3,5,6-tetrahydropyran-4-yl)-1-cyclopropyl-6-fluoro-8-methoxy-1,4-dihydro-4-oxo-3-quinolinecarboxylic acid hydrochloride.

NMR (DMSO-$d_6$) δ: 0.68–1.43 (4H,m), 2.16–2.92 (4H,m), 3.18–4.10 (4H,m), 3.87 (3H,s), 4.10–4.28 (1H,m), 7.88 (1H,d,J=12.67 Hz), 8.88 (1H,s), 8.82–9.05 (3H,brs).
Fab-MS m/e 377 (M+H)$^+$.

Example 19

Synthesis of ethyl 1-cyclopropyl-7-(1-diphenylmethoxycar-bonylcyclobutyl)-6-fluoro-8-methoxy-1,4-dihydro-4-oxo-3-quinolinecarboxylate The procedure of Example 4 was repeated to thereby give ethyl 1-cyclopropyl-7-(1-diphenylmethoxycarbonylcyclobutyl)-6-fluoro-8-methoxy-1,4-dihydro-4-oxo-3-quinolinecar-boxylate.
MS m/e 569 ($M^+$).

Example 20

Synthesis of ethyl 7-(1-carboxycyclobutyl)-1-cyclopropyl-6-fluoro-8-methoxy-1,4-dihydro-4-oxo-3-quinolinecarboxylate The procedure of Example 7 was repeated to thereby give ethyl 7-(1-carboxycyclobutyl)-1-cyclopropyl-6-fluoro-8-methoxy-1,4-dihydro-4-oxo-3-quinolinecarboxylate.
MS m/e 403 ($M^+$).

Example 21

Synthesis of ethyl 7-(1-t-butoxycarbonylaminocyclobutyl)-1-cycloprooyl-6-fluoro-8-methoxy-1,4-dihydro-4-oxo-3-guinolinecarboxylate The procedure of Example 10 was repeated to thereby give ethyl 7-(1-t-butoxycarbonylaminocyclobutyl)-1-cyclopropyl-6-f luoro-8-methoxy-1,4-dihydro-4-oxo-3-quinoline-carboxylate.
NMR ($CDCl_3$) δ: 0.72–2.03 (6H,m), 1.42 (9H,s), 2.34–2.92 (4H,m), 3.73 (3H,s), 3.72–4.06 (3H,m), 7.64 (1H,d,J=11 Hz), 8.55 (1H,s), 9.34 (1H,brs).
MS: m/e 474 ($M^+$).

Example 22

Synthesis of 7-(1-t-butoxycarbonylaminocyclobutyl)-1-cyclo-propyl-6-fluoro-8-methoxy-1,4-dihydro-4-oxo-3-Quinolinecarboxylic acid The procedure of Example 13 was repeated to thereby give 7-(1-t-butoxycarbonylaminocyclobutyl)-1-cyclopropyl-6-fluoro-8-methoxy-1,4-dihydro-4-oxo-3-quinolinecarboxylic acid.
NMR ($CDCl_3$-DMSO-$d_6$) δ: 0.90–1.23 (4H,m), 1.34 (9H,s), 1.90–1.98 (1H,m), 2.09–2.38 (1H,m), 2.56–2.74 (4H,m), 3.82 (3H,s), 4.10–4.25 (1H,m), 7.72 (1H,d,J=10.72 Hz), 8.87 (1H,s).
MS: m/e 446 ($M^+$).

Example 23

Synthesis of 7-(1-aminocyclobutyl)-1-cyclopropyl-6-fluoro-8-methoxy-1,4-dihydro-4-oxo-3-guinolinecarboxylic acid hydro-chloride The procedure of Example 16 was repeated to thereby give 7-(1-aminocyclobutyl)-1-cyclopropyl-6-fluoro-8-methoxy-1,4-dihydro-4-oxo-3-quinolinecarboxylic acid hydrochloride.
NMR (DMSO-$d_6$) δ: 0.96–1.24 (4H,m), 1.90–2.06 (2H,m), 2.60–3.02 (4H,m), 3.87 (3H,s), 4.14–4.30 (1H,m), 7.86 (1H,d,J=10.72 Hz), 8.85 (1H,s).
Fab-MS m/e 347 $(M+H)^+$.

Example 24

Synthesis of ethyl 7-(1-t-butoxycarbonylaminocyclopropvl)-1-cyclopropyl-6-fluoro-8-methoxy-1,4-dihydro-4-oxo-3-guinolinecarboxylate To 394 mg of ethyl 1-cyclopropyl-7-(1-diphenylmethoxycarbonylcyclopropyl)-6-fluoro-8-methoxy-1,4-dihydro-4-oxo-3-quinolinecarboxylate obtained in Example 3, 2 ml of anisole and 2 ml of trifluoroacetic acid were added and the resulting mixture was stirred at room temperature for 1 hour. After concentrating the reaction mixture under reduced pressure, the obtained residue was washed with n-hexane. Then diisopropyl ether was added thereto and the crystals thus precipitated were collected by filtration.

The obtained crystals were dissolved in 5 ml of methylene chloride. Under ice-cooling, 292 mg of diphenyl-phosphoryl azide and 107 mg of triethylamine were added thereto and the resulting mixture was stirred at room temperature for 15 hours. Then the reaction mixture was concentrated under reduced pressure and 10 ml of ethyl acetate and 10 ml of 2N hydrochloric acid were added to the obtained residue. The organic layer was collected, successively washed with water and a saturated aqueous solution of sodium chloride and dried over anhydrous sodium sulfate. After removing the solvent under reduced pressure, 6 ml of t-butanol was added to the obtained residue and the mixture was refluxed for 6 hours. After removing the solvent under reduced pressure, the obtained residue was purified by silica gel column chromatography (eluent: methylene chloride:methanol= 100:3). After recrystallizing from ethyl acetate/n-hexane and filtering, 50 mg of ethyl 7-(1-t-butoxycarbonylaminocyclopropyl)-1-cyclopropyl-6-fluoro-8-methoxy-1,4-dihydro-4-oxo-3-quinolinecarboxylate was obtained (yield: 15.3%).
NMR ($CDCl_3$) δ: 0.72–1.47 (11H,m), 1.32 (9H,s), 3.70–4.10 (1H,m), 3.92 (3H,s), 4.31 (2H,q,J=7 Hz), 5.72 (1H,s), 7.77 (1H,d,J=10 Hz), 8.51 (1H,s).
Fab-MS m/e 461 $(M+H)^+$.

Example 25

Synthesis of 7-(1-t-butoxycarbonylaminocyclopropyl)-1-cyclo-proPyl-6-fluoro-8-methoxy-1,4-dihydro-4-oxo-3-guinolinecar-boxylic acid The procedure of Example 13 was repeated to thereby give 7-(1-t-butoxycarbonylaminocyclopropyl)-1-cyclopropyl-6-fluoro-8-methoxy-1,4-dihydro-4-oxo-3-quinolinecarboxylic acid.
NMR ($CDCl_3$) δ: 0.85–1.60 (8H,m), 1.39 (9H,s), 3.90–4.20 (1H,m), 4.06 (3H,s), 5.66 (1H,s), 7.87 (1H,d,J=11 Hz), 8.88 (1H,s).
Fab-MS m/e 433 $(M+H)^+$.

Example 26

Synthesis of 7-(1-aminocyclopropyl)-1-cyclopropyl-6-fluoro-8-methoxy-1,4-dihydro-4-oxo-3-puinolinecarboxylic acid hydrochloride The procedure of Example 16 was repeated to thereby give 7-(1-aminocyclopropyl)-1-cyclopropyl-6-fluoro-8-methoxy-1,4-dihydro-4-oxo-3-quinolinecarboxylic acid hydrochloride.
NMR ($CD_3$ OD) δ: 0.96–1.34 (4H,m), 1.50–1.72 (4H,m), 4.08 (3H,s), 4.20–4.34 (1H,m), 7.97 (1H,d,J=10 Hz), 8.94 (1H,s).
MS m/e 332 ($M^+$).

Example 27

Synthesis of 1-cyclopropyl-6-fluoro-7-(1-hydroxycarbonyl-cyclopropyl)-8-methoxy-1,4-dihydro-4-oxo-3-quinolinecarboxylic acid 180 mg of ethyl 1-cyclopropyl-6-fluoro-7-(1-hydroxycarbonylcyclopropyl)-8-methoxy-1,4-dihydro-4-oxo-3-quino-linecarboxylate was suspended in 2 ml of ethanol.

After adding 1 ml of 2N NaOH, the mixture was stirred at room temperature for 15 hours. Then 2N HCl was added to the reaction mixture and the organic layer was collected, successively washed with water and a saturated aqueous solution of sodium chloride and dried over anhydrous sodium sulfate. After removing the solvent under reduced pressure, the residue was crystallized from diisopropyl ether and the crystals were collected by filtration. Thus 144 mg of 1-cyclopropyl-6-fluoro-7-(1-hydroxycarbonylcyclopropyl)-8-methoxy-1,4-dihydro-4-oxo-3-quinolinecarboxylic acid was obtained (yield: 86.2%).

NMR (DMSO-$d_6$) δ: 1.00–1.40 (8H,m), 3.91 (3H,s), 4.14–4.30 (1H,m), 7.79 (1H,d,J=9.3 Hz), 8.76 (–1H,s).

Fab-Ms 362 (M+H)$^+$.

Example 28

Synthesis of 1-cyclopropyl-6-fluoro-7-(4-hydroxycarbonyl-2,3,5,6-tetrahydropyran-4-yl)-8-methoxy-1,4-dihydro-4-oxo-3-quinolinecarboxylic acid The procedure of Example 13 was repeated to thereby give 1-cyclopropyl-6-fluoro-7-(4-hydroxycarbonyl-2,3,5,6-tetrahydropyran-4-yl)-8-methoxy-1,4-dihydro-4-oxo-3-quinolinecarboxylic acid.

NMR (CDCl$_3$) δ: 0.56–1.32 (6H,m), 2.15–2.32 (4H,m), 3.68 (3H,s), 3.62–3.88 (2H,m), 4.08–4.25 (1H,m), 7.55 (1H, d,J=12.67 Hz), 8.82 (1H,s).

MS m/e 405 (M$^+$).

Example 29

Synthesis of 1-cyclopropyl-6-fluoro-7-(1-hydroxycarbonyl-cyclohexyl)-8-methoxy-1,4-dihydro-4-oxo-3-guinolinecar-boxylic acid The procedure of Example 13 was repeated to thereby give 1-cyclopropyl-6-fluoro-7-(1-hydroxycarbonylcyclohexyl)-8-methoxy-1,4-dihydro-4-oxo-3-quinolinecarboxylic acid.

NMR (DMSO-$d_6$) δ: 0.58–1.88 (10H,m), 2.04–2.22 (4H,m), 3.65 (3H,s), 4.15 (1H,m), 7.73 (1H,d,J=12.67 Hz), 8.81 (1H,s).

Ms m/e 403 (M$^+$).

Example 30

Synthesis of 7-(1-aminocarbonylcyclohexyl)-1-cyoproPyl-6-fluoro-8-methoxy-1,4-dihydro-4-oxo-3-guinolinecarboxylic acid The procedure of Example 13 was repeated to thereby give 7-(1-aminocarbonylcyclohexyl)-1-cyclopropyl-6-fluoro-8-methoxy-1,4-dihydro-4-oxo-3-quinolinecarboxylic acid.

NMR (DMSO-$d_6$) δ: 0.58–1.60 (10H,m), 1.60–1.88 (2H,m), 1.92–2.13 (2H,m), 3.38–3.54 (1H,m), 3.69 (3H,s), 7.71 (1H,d,J=12.67 Hz), 8.83 (1H,s).

Ms m/e 402 (M$^+$).

Example 31

Synthesis of 7-(4-aminopiperidin-4-yl)-1-cvclopropyl-6-fluoro-8-methoxy-1,4-dihydro-4-oxo-3-guinolinecarboxylic acid hydrochloride The procedure of Example 16 was repeated to thereby give 7-(4-aminopiperidin-4-yl)-1-cyclopropyl-6-fluoro-8-methoxy-1,4-dihydro-4-oxo-3-quinolinecarboxylic acid hydrochloride.

NMR (CD$_3$OD) δ: 0.65–1.55 (4H,m), 2.75–3.80 (8H,m), 3.91 (3H,s), 4.15–4.30 (1H,m), 7.98–8.05 (1H,d,J=14 Hz), 9.01 (1H,s).

Fab-Ms m/e 376 (M+H)$^+$.

Example 32

Synthesis of 1-cyclopropyl-6-fluoro-7-(4-hydroxycarbonyl-piperidin-4-yl)-8-methoxy-1,4-dihydro-4-oxo-3-guinolinecarboxylic acid methanesulfonate To 400 mg of 7-(N-benzyloxycarbonyl-4-diphenyl-methoxycarbonylpiperidin-4-yl)-1-cyclopropyl-6-fluoro-8-methoxy-1,4-dihydro-4-oxo-3-quinolinecarboxylic acid, 10 ml of anisole and 10 ml of trifluoroacetic acid were added. Next, 1.3 ml of methanesulfonic acid was slowly added thereto and the resulting mixture was stirred at room temperature for 62 hours. Diethyl ether was added to the reaction mixture and the crystals thus precipitated were collected by filtration. Thus 130 mg of 1-cyclopropyl-6-fluoro-7-(4-hydroxycarbonylpiperidin-4-yl)-8-methoxy-1,4-dihydro-4-oxo-3-quinolinecarboxylic acid methanesulfonate was obtained (yield: 46%).

NMR (CD$_3$OD) δ: 0.65–1.50 (4H,m), 2.55–3.60 (9H,m), 3.75 (3H,s), 4.15–4.25 (1H,m), 7.80–7.90 (1H,d,J=13 Hz), 8.95 (1H,s).

Fab-Ms m/e 405 (M+H)$^+$.

Example 33

Synthesis of 7-cyclopentyl-1-cyclopropyl-6-fluoro-8-methoxy-1,4-dihydro-4-oxo-3-quinolinecarboxylic acid The procedure of Example 13 was repeated to thereby give 7-cyclopentyl-1-cyclopropyl-6-fluoro-8-methoxy-1,4-dihydro-4-oxo-3-quinolinecarboxylic acid.

NMR (CD$_3$OD) δ: 0.95–1.37 (4H,m), 1.52(4H,brs), 1.65–2.26 (4H,m), 3.53–3.70 (1H,m), 3.78 (3H,s), 3.97–4.08 (1H,m), 7.90 (1H,d,J=10 Hz), 8.88 (1H,s), 14.6 (1H,s).

Fab-Ms m/e 346 (M+H)$^+$.

Example 34

Synthesis of 1-cyclopropyl-6-fluoro-8-methoxy-7-(piperidin-4-yl)-1,4-dihydro-4-oxo-3-quinolinecarboxylic acid methane-sulfonate The procedure of Example 32 was repeated to thereby give 1-cyclopropyl-6-fluoro-8-methoxy-7-(piperidin-4-yl)-1,4-dihydro-4-oxo-3-quinolinecarboxylic acid methanesulfonate.

NMR (CD$_3$OD) δ: 0.80–1.35 (4H,m), 1.90–3.77 (9H,m), 3.77 (3H,s), 4.12–4.30 (1H,m), 7.89 (1H,brs), 8.88 (1H,s).

Fab-MS m/e 361 (M+H)$^+$.

Example 35

Synthesis of 1-cyclopropyl-6-fluoro-7-(3-hydroxy-1-hydroxy-carbonylcyclobutyl)-8-methoxy-1,4-dihydro-4-oxo-3-quinoline-carboxylic acid The procedure of Example 13 was repeated and the obtained residue was treated by the method of Example 16 to thereby give 1-cyclopropyl-6-fluoro-7-(3-hydroxy-1-hydroxycarbonylcyclobutyl)-8-methoxy-1,4-dihydro-4-oxo-3-quinolinecarboxylic acid.

NMR (CD$_3$OD+CDCl$_3$) δ: 0.83–1.18 (4H,m), 1.18–1.47 (4H,m), 3.35 (3H,s), 4.10–4.22 (1H,m), 7.85–8.03 (1H, m), 8.93 (1H,s).
Fab-MS m/e 392 (M+H)$^+$.

Example 36

Synthesis of 7-(1-amino-3-hydroxycyclobutyl)-1-cyclopropyl-6-fluoro-8-methoxy-1,4-dihydro-4-oxo-3-guinolinecarboxylic acid The procedure of Example 35 was repeated to thereby give 7-(1-amino-3-hydroxycyclobutyl)-1-cyclopropyl-6-fluoro-8-methoxy-1,4-dihydro-4-oxo-3-quinolinecarboxylic acid.

NMR (CD$_3$OD+CDCl$_3$) δ: 0.80–1.45 (8H,m), 3.55–3.72 (1H,m), 3.35 (3H,brs), 4.10–4.37 (1H,m), 7.90–8.25 (1H, m), 8.97 (1H,s).

Next, the pharmacological actions of typical examples of the compound of the present invention will be shown.

Test Example 1

Antibacterial activity test

The minimum inhibitory concentrations (MIC) of the test compounds were measured by the publicly known agar plate dilution method. Table 1 shows the results.

TABLE 1

| | MIC | | |
|---|---|---|---|
| | Compd. of Ex. 26 | Compd. of Ex. 23 | Compd. of Ex. 16 |
| S. aureus 209P | 0.39 | 0.78 | 1.56 |
| JU-5 | 0.20 | 0.39 | 0.39 |
| MRSA RN-10 | 0.39 | 0.78 | 1.56 |
| S. epidermidis IFO 12993 | 0.78 | 1.56 | 3.13 |
| B. subtilis ATCC 6633 | 0.05 | 0.10 | 0.10 |
| B. cereus IFO 13494 | 0.20 | 0.78 | 0.78 |
| E. coli NIHJ JC-2 | 0.20 | 0.20 | 0.39 |
| CSJ 1922 | 0.10 | 0.20 | 0.20 |
| S. typhimurium LT-2 | 0.20 | 0.39 | 0.39 |
| C. freundii IFO 12681 | 0.10 | 0.20 | 0.20 |
| K. pneumoniae B-54 | 0.10 | 0.20 | 0.20 |
| E. cloacae IFO 3320 | 0.025 | 0.10 | 0.10 |
| E. aeruginosa IFO 13534 | 0.20 | 0.39 | 0.39 |
| S. marcescens IFO 12648 | 0.20 | 0.78 | 0.39 |
| TO-101 | 0.20 | 0.39 | 0.39 |
| P. vulgaris IFO 3851 | 0.10 | 0.20 | 0.20 |
| P. mirabilis IFO 13300 | 0.05 | 0.39 | 0.20 |
| P. rettgeri IFO 13501 | 0.20 | 0.39 | 0.20 |
| M. morganii IFO 3848 | 0.05 | 0.10 | 0.20 |
| P. aeruginosa GNB-139 | 0.78 | 3.13 | 3.13 |
| X. maltophilia IFO 14161 | 0.78 | 0.78 | 0.78 |
| A. faecalis IFO 13111 | 1.56 | 1.56 | 1.56 |
| A. calcoaceticus IFO 12552 | 0.78 | 1.56 | 0.78 |

Test Example 2

Cytotoxicity test

The 50% inhibitory concentrations (IC$_{50}$) of the test compounds on a mouse lymphatic leukemia cell line L1210 were determined by the MTT [3-(4,5-dimethylthiazol-2-yl)-2,5-diphenyltetrazolium bromide] method.

Namely, 2×10$^4$ L1210 cells were incubated in 200 μl of a culture medium (RPMI-1640 medium containing 10% of fetal bovine serum) containing a two-fold serial dilution of a test compound at 37° C. for a day. Four hours before the completion of the incubation, 10 μl of a 5 mg/ml solution of MTT was added. When the incubation was completed, the culture medium was eliminated by sucking and the insoluble formazan, which had been reduced by the mitochondrial dehydrogenase of the cells, was extracted with 100 μl of dimethylsulfoxide. Then the absorbance was measured at 550 nm. The cell propagation ratio was expressed in the ratio of the formazan formation of the test lot to that of the control lot wherein cells were incubated in a medium free from any test compound. Then IC$_{50}$ was determined by the probit method. Table 2 shows the results.

TABLE 2

| Compound | IC$_{50}$ (μg/ml) |
|---|---|
| Compd. of Ex. 16 | 399 |
| Compd. of Ex. 17 | 399 |
| Compd. of Ex. 18 | >800 |
| Compd. of Ex. 26 | 323 |
| Ofloxacin | 195 |
| Ciprofloxacin | 77 |

Test Example 3

Phototoxicity test

The phototoxicity was determined by enhancing the cytotoxicity of a test compound on L1210 via UV irradiation. Namely, 5×10$^3$ L1210 cells were suspended in 100 pl of Hanks' solution containing 10 pg/ml of the test compound, which showed no cytotoxicity per se, followed by the irradiation with long-wavelength ultraviolet rays (UVA) by using a black light fluorescent lamp. After the irradiation, 100 μl of a culture medium was added and the cells were incubated at 37° C. for 2 days. The result was expressed in the ratio of the formazan formation determined by the MTT method of the test lot to that of the control lot wherein UVA irradiation was not performed. Table 3 shows the results.

TABLE 3

| | Phototoxicity (%; propagation ratio under 0.5 J-irradiation to non-irradiation lot) |
|---|---|
| Compd. of Ex. 26 | >100 |
| Ofloxacin | 69 |
| Ciprofloxacin | 9 |

Industrial Applicability

The fluoroquinoline derivative represented by the general formula (1) or its salt shows an excellent antibacterial activity on both of gram-positive and gram-negative bacteria. When orally or parenterally administered, it achieves a high concentration in the blood. Also, it is a stable chemical having a low toxicity and a high photostability and exhibiting a low cytotoxicity under light irradiation. Accordingly, this compound is highly useful as a drug such as an antibacterial agent.

We claim:

1. A fluoroquinoline derivative represented by the formula (1):

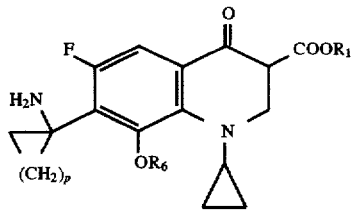
(1)

wherein $R_1$ represents hydrogen or a lower alkyl;

$R_6$ represents lower alkyl; and

P represents 1, 2, 3 or 4.

2. An antibacterial composition comprising an effective amount of an antibacterial compound having the following formula:

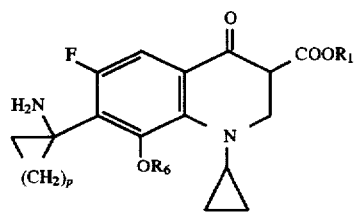

wherein $R_1$ represents hydrogen or lower alkyl;

$R_6$ represents lower alkyl;

P represents 1, 2, 3 or 4;

and a pharmaceutically acceptable carrier.

3. The antibacterial composition according to claim 2 wherein the pharmaceutically acceptable carrier is selected from the group consisting of syrups, granules, ointments, suppository bases, capsules, tablet fillers, eye drops, and dusts.

4. The antibacterial composition according to claim 2 wherein the antibacterial compound is present in an amount to provide a dose of from 0.1 to 100 mg/kg.

5. A method of treating bacterial infections comprising administering to a patient suffering from a bacterial infection an effective amount of an antibacterial composition according to claim 2.

6. The method according to claim 5 wherein the antibacterial composition is administered in a dose of from 0.1 to 100 mg/kg/day.

7. The method according to claim 5 wherein said antibacterial composition is administered parenterally.

8. The method according to claim 5 wherein said antibacterial composition is administered orally.

* * * * *